(12) United States Patent
Hennies et al.

(10) Patent No.: US 7,045,307 B2
(45) Date of Patent: May 16, 2006

(54) METHOD FOR MEASURING NO SYNTHASE ACTIVITY

(75) Inventors: Hagen-Heinrich Hennies, Simmerath (DE); Bernd Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 98 days.

(21) Appl. No.: 10/379,717

(22) Filed: Mar. 6, 2003

(65) Prior Publication Data

US 2004/0002129 A1 Jan. 1, 2004

Related U.S. Application Data

(63) Continuation of application No. PCT/EP01/10151, filed on Sep. 4, 2001.

(30) Foreign Application Priority Data

Sep. 6, 2000 (DE) ............................... 100 43 845

(51) Int. Cl.
*G01N 33/53* (2006.01)
(52) U.S. Cl. ........................ 435/7.72; 435/4; 435/7.1
(58) Field of Classification Search .................... 435/4, 435/7.1, 7.72
See application file for complete search history.

(56) References Cited

U.S. PATENT DOCUMENTS

| 4,058,456 | A |   | 11/1977 | Head | 210/650 |
| 5,629,322 | A |   | 5/1997  | Guthikonda et al. | 514/313 |
| 5,972,975 | A |   | 10/1999 | Esser et al. | 514/352 |
| 2003/0022914 | A1 | * | 1/2003 | Maul et al. | 514/300 |

FOREIGN PATENT DOCUMENTS

| DE | 19902387 A1 | * | 7/2000 |

OTHER PUBLICATIONS

Dawson et al, A microtiter-plate assay of nitric oxide synthase activity. Molecular Biotechnology, 1999, vol. 12, pp. 275-279.*
Gross, S., Microtiter plate assay for determining kinetics of nitric oxide synthesis. Methods in Enzymology, 1996, vol. 268, pp. 159-168.*
McCarty, M., Purification and properties of desoxyribonuclease isolated from beef pancreas. Journal of General Physiology, 1946, pp. 123-139.*
David S. Bredt, et al., "Isolation of Nitric Oxide Synthetase, a calmodulin-requiring Enzyme" Proc. National. Acad. Of Science, vol. 87, Jan. 1990, pp. 682-685.
David S. Bredt, et al., "Nitric oxide mediates glutamate-linked enhancement of cGMP levels in the cerebellum" Proc. National Acad. Of Science, vol. 86, Nov. 1989, pp. 9030-9033.
J. M. Cunningham, et al., "Interleukin-1β-Mediated Inhibition of Arginase in RINm5F Cells" Cytokine, vol. 9, No. 8, Aug. 1997, pp. 570-576.
Richard G. Knowles, et al., "Measurement of NOS Activity by Conversion of Radiolabeled Arginine to Citrulline Using Ion-Exchange Separation" Methods in Molecular Biology, vol. 100, Nitric Oxide Protocols, pp. 67-73.
"Blotting and Chromatography Papers" www.whatman.plc.uk/products/analytical/labfiltration/a_pd_labfil_002.html.

* cited by examiner

*Primary Examiner*—Anne Marie Grunberg
*Assistant Examiner*—June Hwu
(74) *Attorney, Agent, or Firm*—Crowell & Moring LLP

(57) ABSTRACT

A method for measuring the activity of NO-synthase, a corresponding method for identification of NO-synthase modulators, in particular for application in a HTS (High Throughput Screening) and use of the corresponding cation-exchange filter-plate membranes.

44 Claims, 2 Drawing Sheets

Fig. 2

HIT recognition

| | 1 | 2 | 3 | 4 | 5 | 6 | 7 | 8 | 9 | 10 | 11 | 12 |
|---|---|---|---|---|---|---|---|---|---|---|---|---|
| A | MAX<br>20023 ccpm | Object 1<br>10243 ccpm | Object 9<br>5016 ccpm | Object 17<br>5226 ccpm | Object 25<br>4551 ccpm | Object 33<br>4447 ccpm | Object 41<br>4813 ccpm | Object 49<br>5938 ccpm | Object 57<br>4715 ccpm | Object 65<br>5577 ccpm | Object 73<br>3615 ccpm | MAX<br>19867 ccpm |
| B | MAX<br>19667 ccpm | Object 2<br>4395 ccpm | Object 10<br>4663 ccpm | Object 18<br>4326 ccpm | Object 26<br>5167 ccpm | Object 34<br>4490 ccpm | Object 42<br>9814 ccpm | Object 50<br>6821 ccpm | Object 58<br>5374 ccpm | Object 66<br>4343 ccpm | Object 74<br>4054 ccpm | MAX<br>20613 ccpm |
| C | MAX<br>19536 ccpm | Object 3<br>13664 ccpm | Object 11<br>8407 ccpm | Object 19<br>5469 ccpm | Object 27<br>5442 ccpm | Object 35<br>4649 ccpm | Object 43<br>4994 ccpm | Object 51<br>4167 ccpm | Object 59<br>4529 ccpm | Object 67<br>3750 ccpm | Object 75<br>4236 ccpm | MAX<br>18772 ccpm |
| D | MIN<br>3665 ccpm | Object 4<br>5265 ccpm | Object 12<br>4176 ccpm | Object 20<br>4363 ccpm | Object 28<br>3820 ccpm | Object 36<br>4112 ccpm | Object 44<br>4155 ccpm | Object 52<br>4337 ccpm | Object 60<br>3913 ccpm | Object 68<br>3502 ccpm | Object 76<br>4075 ccpm | MIN<br>3620 ccpm |
| E | MIN<br>4308 ccpm | Object 5<br>4653 ccpm | Object 13<br>3695 ccpm | Object 21<br>4074 ccpm | Object 29<br>4822 ccpm | Object 37<br>3957 ccpm | Object 45<br>4131 ccpm | Object 53<br>4941 ccpm | Object 61<br>4430 ccpm | Object 69<br>3737 ccpm | Object 77<br>4131 ccpm | MIN<br>3739 ccpm |
| F | MIN<br>3817 ccpm | Object 6<br>6273 ccpm | Object 14<br>3850 ccpm | Object 22<br>4224 ccpm | Object 30<br>3804 ccpm | Object 38<br>5737 ccpm | Object 46<br>4455 ccpm | Object 54<br>4959 ccpm | Object 62<br>5728 ccpm | Object 70<br>4124 ccpm | Object 78<br>3803 ccpm | MIN<br>3283 ccpm |
| G | Ref.<br>13052 ccpm | Object 7<br>4568 ccpm | Object 15<br>4064 ccpm | Object 23<br>3918 ccpm | Object 31<br>4289 ccpm | Object 39<br>4512 ccpm | Object 47<br>4155 ccpm | Object 55<br>4767 ccpm | Object 63<br>4969 ccpm | Object 71<br>3909 ccpm | Object 79<br>3834 ccpm | Ref.<br>11294 ccpm |
| H | Ref.<br>13797 ccpm | Object 8<br>4147 ccpm | Object 16<br>3466 ccpm | Object 24<br>3866 ccpm | Object 32<br>3922 ccpm | Object 40<br>4137 ccpm | Object 48<br>6057 ccpm | Object 56<br>4163 ccpm | Object 64<br>4592 ccpm | Object 72<br>3806 ccpm | Object 80<br>4135 ccpm | Ref.<br>12645 ccpm |

METHOD FOR MEASURING NO SYNTHASE ACTIVITY

CROSS REFERENCE TO RELATED APPLICATIONS

The present application is a continuation of International Patent Application No. PCT/EP01/10151, filed Sep. 4, 2001, designating the United States of America and published in German as WO 02/20831, the entire disclosure of which is incorporated herein by reference. Priority is claimed based on Federal Republic of Germany Patent Application No. 100 43 845.8, filed Sep. 6, 2000.

FIELD OF THE INVENTION

The invention relates to a method for measuring the activity of NO synthase, a corresponding method for identification of NO synthase modulators, in particular for application in HTS (high throughput screening) and using corresponding cation-exchange filter-plate membranes.

BACKGROUND OF THE INVENTION

It has been a medical knowledge for over 100 years that nitroglycerine can be used in the treatment of coronary heart disease. It was only recognized 15 years ago, however, that this effect is attributable to the formation of nitric oxide (NO). Since then the significance of this molecule has been visible in an ever-increasing number of publications. Therefore ways of synthesizing NO, and particularly the discovery of compounds which modulate NO synthesis, are of great importance, particularly with regard to pharmacology.

NO is formed by NO synthases (EC: 1.14.13.39) (hereafter sometimes abbreviated to NOS). NOS catalyzes the oxidation of L-arginine to L-citrulline and NO via the intermediary $N^G$-hydroxyarginine. NO synthases have a monomeric molecular mass of between 125 and 155 kDa, but are active only as homodimers. The molecular structure of the NO synthases strongly resembles that of the cytochrome P450 reductases. Various classes of NO synthases are known:

NOS inducible by cytokines or LPS (iNOS), and
constitutive NOS (cNOS), activated by $Ca^{2+}$, which are further subdivided into the following subforms:
endothelial NOS=eNOS
neuronal NOS=nNOS.

In the literature there are many examples of how to determine quantitatively the activity of known NOS isoenzymes. The following methods are the most well known:

1. Separation of the End Product Citrulline Using Column Chromatography

(1)

On completion of the reaction the enzyme mixtures are passed over separate cation exchange columns. Elution of the [$^3$H]L-citrulline and determination of the eluates then takes place on a β-counter. The disadvantage of this method is that column chromatography has to take place separately for each enzyme mixture (e.g. 96 chromatography columns are needed per 96 well microtiter plate). See e.g., D. S. Bredt and S. H. Snyder, Proc. Natl. Acad. Sci. 87, 682 (1990).

2. $NO_2$ Determination Using "Griess Reagent"

In the NOS reaction (see reaction 1) NO is obtained as an end product as well as L-citrulline. NO is, however, unstable and thus continues to react:

$$2\ NO + O_2 \rightarrow 2\ NO_2$$

$$2\ NO_2 + H_2O \rightarrow NO_2^- + NO_3^- + 2H^+ \quad (2)$$

The $NO_3^-$ obtained must be reduced to $NO_2^-$. This can be achieved with cadmium or enzymatically by adding nitrate reductase. Since excess NADPH from the NOS mixture interferes with the Griess reaction with $NO_2^-$, these reduction products must be removed. This can be done enzymatically by adding lactate dehydrogenase/pyruvate. After addition of the Griess reagent (1% sulphanilamide: 0.1% naphthylenediamine dihydrochloride, 5% $H_3PO_4$) a purple-colored AZO dye is produced, which can be determined at 543 nm.

The Griess reaction takes place as follows:

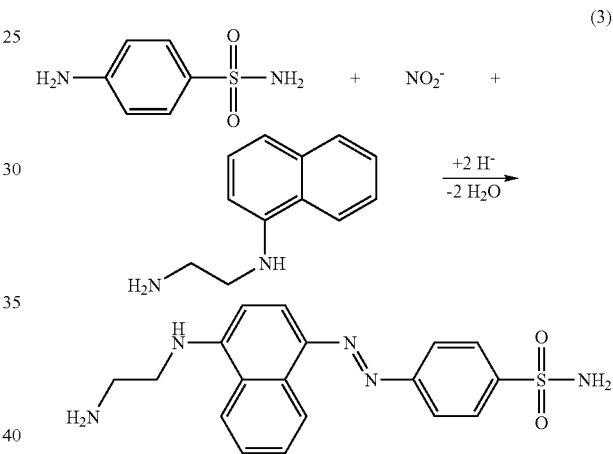

(3)

(Green et al., Anal. Biochem., 126:131 (1982))

The disadvantage of this measuring method is that a plurality of separate reaction steps which must be carried out in sequence are necessary to determine NOS activity.

3. Measurement of Chemiluminescence

The NO obtained and L-citrulline in the NOS reaction react to form $NO_2^-$ and $NO_3^-$ (see reaction 2). However, to measure chemiluminescence $NO_2^-$ and $NO_3^-$ have to be converted back to NO. Then a reaction with ozone is carried out:

$$NO + O_3 \rightarrow NO_2^* + O_2$$

$$NO_2^* \rightarrow NO_2 + h\nu \quad (4)$$

(Archer, FASEB Journal, 7, 349 (1993)).

The disadvantage of this method is that a plurality of reaction steps are also needed. Furthermore, the generation of ozone is costly, which has to be produced particularly for the reaction because of its short half-life.

4. Determination of cGMP Using Guanylate Cyclase which can be Stimulated by NO.

Here the activity of guanylate cyclase can be determined from the quantity of cGMP. Since the, guanylate cyclase is activated by NO, the quantity of NO which is produced, and accordingly the activity of the NOS, can be extrapolated (Feelish et al., Eur. J. Pharmacol. 139:19 (1987); Mayer et al., Biochem. Biophys. Research Commun., 164:678 (1989)).

The disadvantage of this method is that it requires a coupled enzyme reaction. Coupled enzyme reactions usually do not permit the measurement of an initial rate because a clear linear determination of the reaction rate requires the substrates be present in concentrations close to enzyme saturation (~100 $K_m$). This can be a significant cost factor. Moreover, the activity of the guanylate cyclase is not constant in this reaction, as it is only stimulated by NO formed during the coupled reaction.

In modern pharmaceutical research, it is necessary to carry out a considerable number of measurements within the shortest possible time, in particular when testing large numbers of substances, known as libraries, so-called HTS processes (high throughput screening processes) are implemented to screen for individual substances with possible physiological effect. Test procedures used in HTS processes should be able to be automated, be as simple and as fast as possible and, in particular, only require a minimum of simple automatable process steps which do not require manual steps in between. A "rough method" delivering only a yes or no answer is sufficient, so measurements of linear initial rate of an enzyme reaction are not necessary. Time-consuming manipulations such as removal of aliquots, further incubations using coupled (enzyme) reactions, centrifugation steps which can not be automated etc., are automatically ruled out for an HTS operation. At the same time, however, the tests must provide reliable results. Therefore, the precision of the assay is of crucial significance for carrying out an HTS operation, i.e. the "signal to noise ratio" should be as high as possible, so that the precision of the result does not have to be won at the expense of two, three or four determination steps, which, in turn, hamper high volume throughput.

None of the reactions 1–4 presented above, thus, is suitable for HTS, because the coupled enzyme reactions, removal of aliquot parts, centrifugation steps, column chromatography separation steps etc. hamper high throughput screening. The time or number of process steps required to achieve the necessary precision is too great for an HTS process and the procedures are substantially not automatable.

The object of the present invention was, therefore, to develop a simplified method for measuring the activity of NO synthase, in particular also a method for identifying NO synthase modulators. This method should, in particular, be suitable for application in HTS.

SUMMARY OF THE INVENTION

This object is achieved using a method for measuring the activity of NO synthase, with the following process steps:

(a) incubation of the NO synthase with labeled arginine as the substrate in a reaction vessel, (b) separation of the labeled arginine from the labeled citrulline possibly formed as a product of the enzymatic reaction at a moment when the concentration of citrulline is rising, (c) measurement of the amount of arginine separated in each case, wherein the separation is effected by means of a filter-plate membrane.

BRIEF DESCRIPTION OF THE FIGURES

FIG. 2 is the layout of the MTP used in FIG. 1.

DETAILED DESCRIPTION OF THE INVENTION

Figure 1:
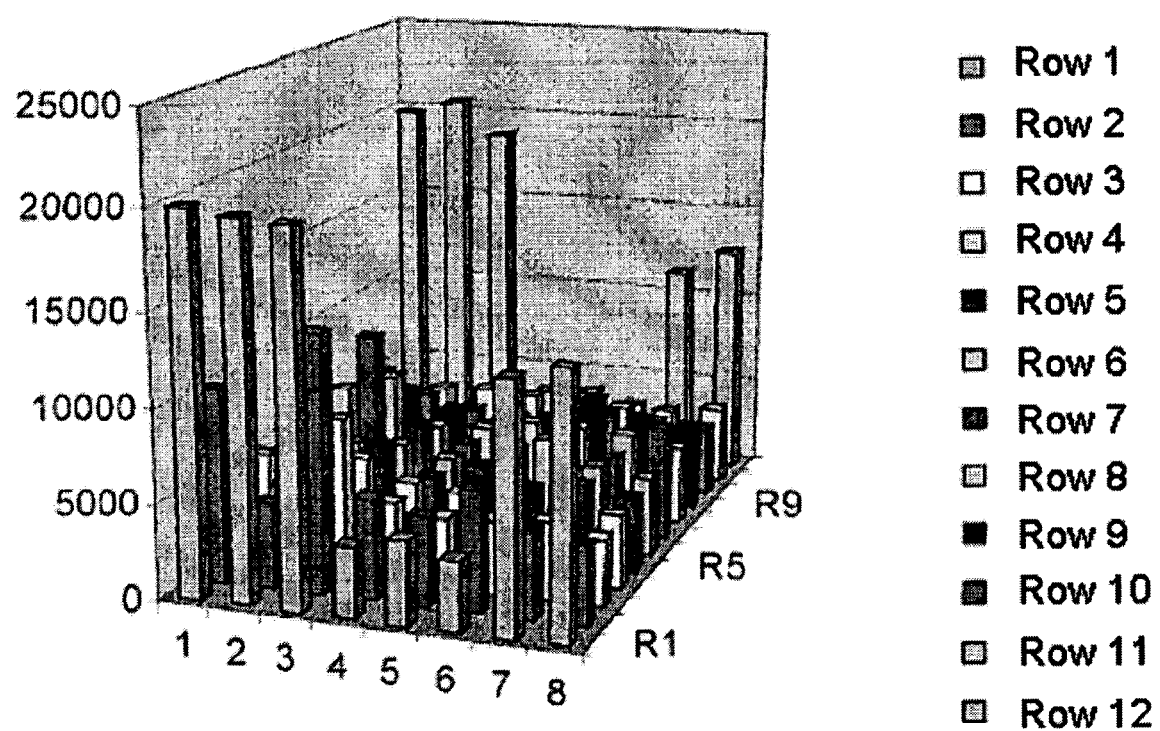
FIG. 1) is a graph showing the result of a screening assay according to Example 4, and relates to FIG. 2. Here the x and y axes correspond to the alphanumeric division of a 96 well microtiter plate (MTP) and the z axis corresponds to the "corrected counts per minute" (ccpm) measured, i.e. the radioactive decay per minute counted in the counter, corrected by zero value and quench factor.

In the context of the present invention the following definitions apply:

Incubation: the introduction and leaving of a biological object, such as an enzyme, NOS, in a medium to which, possibly, further compounds are or have been added, such as the enzyme substrate. For this incubation appropriate (usually similar to physiological) conditions are chosen, in order to achieve a certain effect. For example, an enzyme reaction takes place, e.g., the conversion of arginine into citrulline and NO catalyzed by NOS. The conditions are achieved, for example, by controlling the temperature, pH, coenzymes or cofactors and/or reaction time etc.

Reaction vessel: a vessel in which a chemical reaction, or a separation based on bonding or other physical forces, can take its course under controlled conditions. Examples include an Eppendorf cup, a culture dish or flask, a test tube, a centrifuge tube or a well of a microtiter plate. A reaction vessel may be divided into compartments by selectively permeable membranes. It does not necessarily have to be sealed so that fluids cannot pass through, not even on the underside of the vessel. Thus reaction vessels can be columns or microtiter plates also sealed on one side (usually the underside) by a selectively permeable membrane, such as a filter-plate membrane. The incubation (step a), and preferably also the separation (step b), takes place in a reaction vessel.

Separation: by this the spatial separation of arginine from citrulline is understood, so that, unlike the incubation mixture which contains both substances homogeneously in a certain proportion, separate areas are formed so that the arginine is almost completely confined in one area and the citrulline has almost been completely removed in comparison to the previous concentration, and in an other area the opposite is the case. The separation can, for example, be effected physically by means of size or molecular weight filters, by means of charging (cation exchangers, chromatographically or by applying voltage), or, for example, by centrifugation. In the case according to the invention, separation is effected by means of a filter-plate membrane.

Labeled: labeling is understood to mean making a molecule measurable, for example, by coupling it to another molecule to help generate a measuring signal (e.g. fluorescence, luminescence, metallic ion coupling), or by using radioactive atoms in its synthesis (radioactive labelling).

Moment when the concentration of citrulline is rising: by this a moment is meant when the reaction is still in the process of reacting to form citrulline, so no end point has been reached.

Measurement: in this context measurement is understood to be the quantification of the labeled substance using an appropriate apparatus.

Filter-plate membrane: this is a flat membrane, an interface with a defined permeability, capable of filtering fluids and reclaiming certain substances contained in the fluid.

In a preferred embodiment, the present invention provides this object using a method for measuring the activity of NO synthase, with the following process steps:

(a) incubation of the NO synthase with labeled arginine as the substrate in a reaction vessel, (b) separation of the labeled arginine from the labeled citrulline possibly formed as a product of the enzymatic reaction at a moment when the concentration of citrulline is rising, (c) measurement of the amount of arginine separated in each case, wherein the separation is effected by means of a filter-plate membrane.

The method chosen in this case was to separate the substrate from the end product by means of a filter-plate membrane, allowing a quantitative separation between substrate and the end products to take place in one simple filtration step, without having to collect individual elution fractions. High precision is achieved by means of this simple "filtration step" and it is no longer necessary for determination to take place two or three times. It is the introduction of this filter-plate membrane which permits the method to be successfully applied, for example, in HTS, but also for simple, uncomplicated determinations of NOS activity in general. Labeled L-arginine is particularly preferred as the substrate, and, amongst other things, leads to the formation of labeled L-citrulline as a product.

For comparative purposes, IC50 values of various known NOS inhibitors were also determined using the method according to Bredt and Snyder (1990) (discussed supra in the Background of the Invention). The comparative analysis showed that, in spite of its simple construction, the method according to the present invention is valid and, surprisingly, can compete thoroughly on a qualitative level with the complex, standard column chromatograph method of Bredt and Snyder (1990).

It is particularly preferred, if the method is carried out in such a way that, in at least one of the reaction vessels, a substance is added to the incubation mixture in step (a), and is tested to establish whether it is a modulator, in particular an activator or inhibitor, preferably an inhibitor of NO synthase. Thus the use includes a screening assay by which substances are tested for their physiological effectiveness. Modulator means, in the context of the present invention, a molecule which influences the behavior of a NOS, in particular leading to increased activity (activator) or reduced activity (inhibitor) or even to complete inhibition.

The invention also relates, in particular, to a method for identification of NO synthase modulators, having the following process steps:

(a) Incubation of a substance to be tested under appropriate conditions with NO synthase and labeled arginine in a reaction vessel.

(b) Separation of the labeled arginine from the labeled citrulline possibly formed as a product of the enzymatic reaction at a moment when the concentration of citrulline is rising, (c) Measurement of the amount of arginine separated in each case, wherein the separation is effected by means of a filter-plate membrane.

Further, a "substance to be tested" is understood to be, in particular, a low molecular compound, whose effect on NOS activity is to be tested.

Preferably, the present invention provides a screening process, by which substances, for example from a library, can be identified, which are modulators of NOS and thus potentially pharmacologically interesting compounds. It is particularly preferred, if the method serves to identify an activator or inhibitor, preferably an inhibitor of NO synthase.

Further, in a preferred embodiment of the method according to the invention, in the separation according to step (b), the incubation medium is removed from the reaction vessel. By incubation medium is meant a medium, in which the incubation according to step (a) takes place, and in which the substrate (labeled arginine), NOS, the products formed (labeled citrulline and NO) and their secondary products, and coenzymes or cofactors are dissolved, and which, together with these dissolved or possibly suspended substances, forms the incubation mixture according to step (a). It is particularly preferred if the incubation medium is substantially, in particular almost completely, and preferably completely removed.

When removal is via a filter-plate membrane, "substantially" means that only small drops of the medium are left, "almost completely" means that only the filter-plate membrane contains small amounts of incubation medium, and "completely" means that the medium is either eluted from the filter-plate membrane or removed by drying. Further, it is preferred that the labeled arginine is separated from the incubation medium when the incubation medium is removed.

According to the present invention secondary products are understood to be further products formed by the products, e.g. $NO_2^-$ or $NO_3^-$. A coenzyme is a low molecular, non-protein compound, needed as a co-substrate only temporarily and loosely bound to an enzyme, e.g.: NADPH. Cofactors is a collective term for low molecular substances, whose presence is or can be necessary for enzymatic reactions, e.g. $Ca^{2+}$, and calmodulin.

In the context of the separation according to step (b) it is further preferred that cofactors or coenzymes, the NO synthase, NO and the secondary products are also separated from the labeled arginine. By this is meant the separation of the substances, other than the substrate, added to the incubation medium in the incubation solution according to step (a). Since these substances are usually soluble in water, their removal predominantly coincides with the removal of the incubation medium.

It is particularly preferred that the filter-plate membranes used in the method are cation exchangers. Cation exchangers are materials, e.g., a membrane which, in the exchange process, take in the same quantities of foreign cations from fluids in exchange of cations on the membrane. Further, the filter-plate membranes can preferably be paper or textile filters, or consist of or contain other porous or perforated solid materials, such as metal, glass or ceramics. Examples for the latter include metal foil sieves or filters or clay or glass filters are meant, either uncoated or coated, for example, with gel or resin. Further it is preferred that the functional groups for cation exchange are fixed to the filter-plate membranes. These functional groups are negatively charged groups which serve as a binding point for the cations and are bound covalently, for example, but also possibly by strong ionic bonds, to the carrier.

Preferred functional groups used in the cation exchange filter-plate membranes are phosphate, carbonate, phosphonate, sulfate and/or sulphonate groups, preferably phosphate groups.

Further, if paper filters are used, the thickness of the filter-plate membranes is about 10.00 mm to 0.10 mm, preferably 1.00 mm to 0.15 mm, in particular 0.50 mm to 0.20 mm, preferably 0.23 mm. It is further preferred that the filter-plate membranes are cation exchangers having an exchange capacity of $\geq 1.0$ µEq./cm$^2$, in particular $\geq 10.0$ µEq./cm$^2$, preferably $\geq 18.0$ µEq./cm$^2$. In addition these filter-plates can have a flow rate of $\geq 100$ mm/30 min, preferably 125 mm/30 min.

In a particularly preferred embodiment of the method according to the invention step (a) takes place in a plurality of reaction vessels almost simultaneously, preferably simultaneously, and/or step (b) takes place in a plurality of reaction vessels almost simultaneously, preferably simultaneously, particularly in respect of the beginning of the incubation in step (a) and/or the beginning of the separation according to step (b). It is particularly preferred that the reaction vessels are connected and, in particular, are the wells of a microtiter plate. Microtiter plates which are particularly suitable for use in the method according to the invention, are those having <96 wells, preferably 24 or 48 wells, or $\geq 96$ wells, particularly 96, 384, 864 or 1536 wells.

Further, it is preferred if the reaction vessels utilized for step (a) and/or step (b) in the method according to the invention have the capacity to hold $\leq 2$ ml, in particular $\leq 1$ ml, preferably $\leq 1$ ml, $\leq 800$ µl, $\leq 350$ µl, $\leq 300$ µl, $\leq 250$ µl, $\leq 200$ µl, $\leq 150$ µl, $\leq 100$ µl, $\leq 50$ µl, $\leq 30$ µl or $\leq 5$ µl.

In a particularly preferred embodiment of the method according to the invention, the separation according to step (b) is effected by suction of the incubation medium from step (a) through the filter-plate membrane. A vacuum is applied to the filter-plate membrane on the opposite side to the incubation mixture. In a further, particularly preferred embodiment of the method according to the invention, the fraction containing the labeled citrulline separated from the labeled arginine is discarded after the separation according to step (b). By fraction a part of the incubation mixture present before the separation is meant, in this case incubation medium with certain dissolved portions. Here that is the part of the medium in which the labeled citrulline from the incubation mixture is substantially completely present, and the labeled arginine of the original incubation mixture is (almost) no longer present. Particularly the two latter embodiments substantially simplify the management and automation of the test and make it particularly suitable for HTS.

In yet another preferred method according to the invention, the substrate separated after the separation according to step (b) is present on or in the filter-plate membrane, and the substrate is preferably bound.

It is particularly preferred if the labeling permits measurement of the substrate by means of radioactivity, fluorescence, luminescence or spectrum or color change. In a particularly preferred embodiment measurement of the substrate is carried out in the scintillation counter after scintillation fluid has been added to the filter-plate membrane. In an particularly preferred process step, after separation according to step (b) the filter-plate membrane on which the labeled arginine is present is dried, for example in a drying chamber, either individually or microtiter plate containing a plurality of filter-plate membranes as a whole. Microtiter plates (MTPs) are subsequently sealed, on the bottom. Individual filter membranes, however, are transferred into scintillation vessels. Scintillation fluid is then poured over the filter-plate membranes, and they are sealed (MTPs are sealed on the front) and counted in a scintillation counter.

In a further embodiment of the method, step (a) and step (b) do not take place in the same reaction vessel. This variant is also well suited for HTS. According to this embodiment, the incubation mixture according to step (a) is transferred into a further vessel, which, for example, contains the filter-plate membrane, and in which step (b) takes place. Thus, for example, the incubation mixtures are transferred in parallel from one microtiter plate into another, whose wells contain a filter-plate membrane on the base, for example in the form of a cation exchanger, the filter-plate membrane being fixed in place by a sieve which is permeable to fluid. Here the separation can then, for example, take place by applying a vacuum to the underside of the filter-plate membrane, causing the incubation medium together with, for example, the labeled citrulline to be sucked out and the labeled arginine to remain on or in the filter-plate membrane on the base of the wells.

A further embodiment of the method according to the invention provides for elution after separation according to step (b), preferably $\leq$ three times, particularly once, preferably with water or buffer solution, in particular with a volume of $\leq 10$ ml, particularly $\leq 5$ ml, preferably $\leq 3$ ml, particularly $\leq 2$ ml. The volume of elution fluid depends on the amount per separated (step b) incubation mixture according to step (a), preferably therefore per reaction vessel. This also can bring benefits for application in HTS and, in particular, increase the accuracy of the test. According to this embodiment, the volume of eluant can be significantly higher than the volume of the reaction vessel, as long as fluid is removed again, for example by suction, at the same time as elution fluid is added. If this is not the case, the volume of eluant corresponds preferably to the maximum volume of the reaction vessel in which step (b) is carried out.

In a preferred embodiment of the method it is provided that recombinant NO synthase is used as the NO synthase, and that the NO synthase is, in particular, subtype-specific, preferably a human-, rat-, or mouse-specific eNOS, iNOS or nNOS, in particular also α- or β-nNOS. In this embodiment recombinant NOS is understood to be an NOS which is produced by manipulation using gene technology. A recombinant DNA construct, for example a cloning or rather an expression vector is constructed, for example from the sequence of a cloned NOS gene. This vector is then placed in a cell and, under special cultural conditions, the cell subsequently expresses the gene and forms the protein, i.e., a recombinant NOS.

The following definitions apply:
- (recombinant) DNA construct: general term for all types of DNA molecules which are formed by in-vitro combination of DNA molecules.
- cloning vector: general term for nucleic acid molecules which, in cloning, act as carriers of foreign genes or parts of these genes.
- expression vector: term for specially constructed cloning vectors, which, after insertion in an appropriate host cell, allow transcription and translation of the foreign gene cloned in the vector.

The NO synthase used in the method according to the invention may be a part of a raw extract (hereafter sometimes called NOS raw extract) of vertebrate tissue, preferably mammal tissue. In this method the raw extract can be obtained from rodents and/or from the CNS and/or from supernatant obtained from homogenate, in particular supernatant of a homogenate of rat or mouse cerebellum. Tissue, preferably the cerebellum, is taken from the CNS (central nervous system) of a rodent, preferably a rat or a mouse, and homogenized, centrifuged and the supernatant used as neuronal NOS raw extract. An illustration of such a production method is given in the examples.

Further, it is preferred, that the amount of protein used in the incubation mixture in the method according to step (a) be $\leq 5.0$ µg, particularly $\leq 2.5$ µg, preferably $\leq 1.0$ µg per mm$^2$ of the filter-plate membrane used in step (b). The given quantities of protein are those above which, from experience, the filter-plate membrane can become blocked during the separation, particularly if suction is used.

In addition to the substrate and coenzyme NADPH, isolated NOS (including recombinant enzyme) further requires other coenzymes/cofactors such as tetrahydrobiopterin (BH$_4$) FAD, FMN, calmodulin (CaM) and Ca$^{++}$ (Hobbs et al., Annu. Rev. Pharmacol. Toxicol. 39:191 (1999)). Therefore, it is preferred that in a method according to the invention cofactors or coenzymes and/or NADPH are added to the incubation mixture according to step (a). In particular calmodulin, Ca$^{2+}$, tetrahydrobiopterin, FAD and or FMN can be added to the incubation mixture.

In order to minimize costs in an HTS, the previously mentioned NOS raw extract can be used as an alternative, so that the addition of coenzymes or cofactors such as BH$_4$, CaM, FAD and FMN can be eliminated. Therefore, when using the NOS raw extract described above, NADPH and Ca2+ are added as sole cofactors or coenzymes to the incubation mixture.

It is further preferred that, in the method according to the invention, the incubation mixture is placed in a buffer as an incubation medium. The incubation in step (a) preferably takes place at room temperature, 37° C., 25° C., 10° C. or 4° C., more preferably room temperature.

It is particularly preferred that if the separation according to step (b) takes place 1–600 min, particularly 3–120 min, preferably 5–60 min after the beginning of the incubation according to step (a). These times depend in particular on the activity of the NOS used.

A particularly preferred embodiment of the method according to the invention is suitable for HTS, i.e. it is, in particular, simple, reproducible and also easily automatable.

A decisive criterion for the quality of an assay, in particular for HTS, is the "signal to noise ratio"—the ratio between the low measurement signals and the average background noise (without signal). A particularly good ratio should be aimed for in this respect. This is the case in the methods according to the invention, which have a "signal to noise ratio" of $\geq 4$, in particular $\geq 5$, preferably $\geq 6$ or $\geq 10$.

Methods of the present invention may also be used to measure NOS activities where substrates other than arginine are involved.

It is particularly preferred that this method serves to measure the activity of NO synthase and/or to identify NO synthase modulators, in particular activators or inhibitors, in high throughput screening.

The following examples and figures are intended to clarify the invention, without restricting the subject of the invention to this examples and figures.

EXAMPLES

Example 1

General Method for an HTS NOS Assay

In an HTS NOS assay, radioactive arginine is used as the substrate. The assay volume can be selected according to the type of microtiter plate (MTP) from the range between 25 µl and 250 µl. Cofactors and coenzymes are added depending on the enzyme source used. The incubation of the mixtures in this microtiter plate (the assay MTP) according to step (a) takes place at room temperature and lasts between 5 and 60 minutes, depending on the enzyme activity (units) used. At the end of the incubation (step (a)), the plate is placed in a cell harvester, which is equipped with an MTP having a cation exchange membrane as a filter base (filter MTP). All mixtures from the assay MTP are transferred into this filter MTP and sucked through a cation exchanger filter plate—a paper filter charged with phosphate groups. The filter MTP is subsequently washed with buffer solution or water. Using this method the remaining substrate, arginine, is bound on the cation exchanger while the enzymatically formed radioactive citrulline is quantitatively eluted. After drying the filter MTP and adding scintillation fluid the bound arginine can be counted out on the scintillation counter. A non-inhibited NOS reaction is reflected by low radioactivity. An inhibited enzyme reaction means that the radioactive arginine has not been converted. This means that high radioactivity is found on the filter.

The assay can be run with very low substrate concentrations (e.g. 50 nM). Even under these conditions the "signal to noise ratio" is still over 6. By using higher substrate concentrations a ratio of more than 10 can be achieved. Depending on the available HTS plant several thousand compounds of a library can be screened in only a few days owing to this extremely simple method. This is because the contents of an assay MTP are sucked through only one filter plate containing cation exchanger.

Example 2

Examples of Materials Used arginine, L-[2,3,4-$^3$H]monohydrochloride; order no. NET-1123, NEN
anhydrous CaCl$_2$; order no. 2388.1000; Merck
1.4 dithiothreitol (DTT), order no. 708984; ROCHE
Na$_2$EDTA dihydrate; order no. 03680; FLUKA
HEPES, order no H-3375; SIGMA
NADPH, tetrasodium salt; order no. 1585363; ROCHE
TRIS; Order no. 903349; FLUKA

| | |
|---|---|
| Enzyme preparation buffer: | 50 mM Tris-HCl with 1 mM EDTA: the pH of the buffer is adjusted at 4° C. to 7.4. |
| Incubation buffer (or medium) | 50 mM HEPES with 1 mM EDTA; 1.25 mM CaCl$_2$ and 1 mM dithiothreitol. The pH of the buffer is adjusted at 25° C. to 7.4. |
| Elution medium: | H$_2$O |

Example 3

Enzyme Preparation

Rat cerebella are used as the source tissue. 1 ml of enzyme preparation buffer (4° C.) is added per rat cerebellum. The animals are anaesthetized and put down, the brain tissue (cerebellum) is removed and broken down with a polytron homogenizer for 1 min at 6,000 r.p.m., followed by centrifugation at 4° C. for 15 minutes with 20,000 g. The supernatant is decanted and frozen in portions at –80° C. The precipitate is discarded.

The tissue supernatant containing nSOS remains stable under these conditions for a long time but should only be thawed once, and not be refrozen.

Example 4

This is an Example of an HTS NOS Assay Using Methods Described in Examples 1 to 3 a) Incubation Mixture (Step (a))

96 well MTPs with a well capacity of $\leq 250$ µl are used

Pipetting sequence, see Table 1:

TABLE 1

| Substance | Molarity in mixture | µl | *Protein in mixture: |
|---|---|---|---|
| Incubation buffer | — | 100 | — |
| Test substance | variable, preferably $10^{-5}$ M | variable, preferably 20 µl | |
| NADPH | 0.5 mM | 20 | |
| Enzyme (see Example 3) | — | variable; maximum volume of enzyme mixture = 50 µl | variable; maximum amount of protein permitted = 100 µg |

TABLE 1-continued

| Substance | Molarity in mixture | µl | *Protein in mixture: |
|---|---|---|---|
| [$^3$H] substrate | variable; preferably 50 nM | variable; preferably 10 µl | |
| End volume: | | max. 250 µl | |

*Protein determination according to Lowry et al., J. Biol. Chem., 193, 265 (1951)

After pipetting is complete a lid is placed on this MTPs (assay MTPs). Incubation is at 25° C., i.e. room temperature (RT), for 5–60 minutes, depending on the amount and activity of the enzyme used.

b) Suction Step (Step (b))

The contents of the assay MTPs are then transferred, for example using a 96 well cell harvester, to a 96 well cation exchanger MTP (filter MTP) and sucked out. This is followed by a single elution with 200 ml $H_2O$ (from a tub).

c) Measuring Step (Step (c))

The plate is then dried for one hour at 60° C. in the drying chamber. Then the bottom of the filter MTP is sealed carefully from below with a "back seal." After that 35 µl of scintillator fluid per well is added by pipette. In addition the top of the plate is sealed with a top seal at this point. After one hour the plate can be measured on a β-counter. Measurement can also take place much later, as the measuring signal remains stable.

In the HTS operation it is recommended that the incubation medium, NADPH- and the enzyme mixture are combined before the pipetting step begins, to avoid the need for three separate pipetting steps, which take more time. The assay volume can also be made smaller as long as the concentrations are the same.

Example 5

This is an Application of a Method According to Examples 2–4 in the Screening

The following equipment was used:

TABLE 2

| | |
|---|---|
| Serocluster ® | microtiter plate for the incubation (assay MTP): Costar ®, 96 well, polypropylene, round bottom, cat. no. 3794 (Corning Costar Corporation, Cambridge, MA) |
| Unifilter ® | Cation exchanger filter plate in microtiter plate (filter MTP): Whatman ®, 96 wells, 150 µl, mesh bottom. P81 cellulose phosphate paper, cat. no. 7700-0512 (Whatman Inc., Clifton, NJ) Physical properties: Exchange capacity: 18.0 µEqu./cm$^2$ Flow rate: 125 mm/30 min Thickness: 0.23 mm |
| Brandel ® | 96 well cell harvester, type MPXRI-96T (Brandel, Gaithersburg, MD) |
| Wallac ® | Trilux 1450 Microbeta, liquid scintillation and luminescence counter (Wallac-ADL-GmBH, D-79111 Freiburg, Germany) |
| Enzyme | Preparation of rat cerebelli, see Example 3 |
| TopSeal ™ | Packard (Packard, Meriden, CT) |
| BackSeal | Packard company Packard, Meriden, CT |
| Scintillator | Type: Ultima Gold ™ (Packard, Meriden, CT) |
| Test substances: | $1 \times 10^{-5}$ M in mixture |
| Internal standard: | 7-nitroindazole, $1 \times 10^{-5}$ M in the mixture |
| NADPH: | 0.5 mM in the mixture |
| [$^3$H] substrate: | 50 nM in the mixture |
| Incubation time: | 30 min at room temperature |

All other parameters and process steps to be carried out as before (see Example 4.)

FIG. 2 shows a series of experiments, in which 80 substances were tested Positions A2–A11; B2–B11; C2–C11; D2–D11; E2–E11; F2–F11; G2–G11 and H2–H11). The alphanumeric division in this table corresponds to that of a 96 well microtiter plate and the corrected counts per minute (ccpm) are given, i.e. the radioactive decay counted on the counter, corrected by zero value and quench factor.

Complete mixtures, without enzyme however, show the 100% [$^3$H]arginine initial content. ("Max"=positions A1; B1; C1; A12; B12; C12).

The conversion to [$^3$H]citrulline and NO can be seen in complete mixtures (with enzyme) because the [$^3$H]arginine content is lower ("min"=minimum [$^3$H]arginine content=uninhibited enzyme reaction; positions D1, E1; F1; D12; E12 and F12). This can, however, be exceeded with NOS activators, since there even more arginine is converted than with unmodulated enzyme, so that even less radioactivity remains on the filter.

As an internal standard (reference) the NOS inhibitor 7-nitroindazole was used in a concentration of $1\times10^{-5}$ M ("Ref"=G1; H1; G12 and H12)

Test of 80 substances in NOS assay in 96 well microtiter plate format

Of the 80 compounds tested, 3 show NOS inhibition (positions A2; C2 and B7; N=1)

The mean value for the reference substance 7-nitroindazole (=internal standard, $1\times10^{-5}$M in mixture) is:

$\bar{x}=12\,697\pm1\,050$ ccpm ($\bar{x}\pm SD$; N=4)

This 7-nitroindazole concentration was chosen specifically to be in the range of about 50% inhibition.

The mean value of the "max" data (without enzyme, reference value for 100% [$^3$H] arginine) is represented as follows:

$\bar{x}=19\,746\pm607$ ccpm ($\bar{x}\pm SD$; N=6)

The mean value of the "min" data (uninhibited enzyme reaction) yields the following radioactivity:

$\bar{x}=3\,158\pm334$ ccpm ($\bar{x}+SD$; N=6)

Thus in this example 16 588 ccpm (19 746–3 158 ccpm) are available for measurement in total.

Example 6

Comparison between Method of the Present Invention and that of Bredt & Snyder (1990) for Measuring the IC50 of a Plurality of Reference Substances The measurement of citrulline using column chromatography was carried out according to the description of D. S. Bredt and S. H. Snyder, Proc. Natl. Acad. Sci. 87, 682 (1990), in which the substrate [$^3$H]arginine was present in the mixture in a concentration of 50 nM, and the enzyme was isolated nNOS from rat cerebella, as described in Example 3. The separation was effected by means of column chromatography.

The procedure according to the invention corresponded to the procedure according to Example 4, in which the substrate, [$^3$H]arginine, was also present in the mixture in a concentration of 50 nM and the enzyme was isolated nNOS from rat cerebella, as described in Example 3. The separation was effected according to the invention by means of 96 well cation exchanger multititre plates (MTP/filter MTPs).

The following known NOS inhibitors were employed as test substances to determine the IC50 values in a plurality of concentrations in the two tests undergoing comparison:

7-nitroindazole,
1-(2-trifluormethylphenyl)imidazole (=TRIM)
$N^G$ monomethyl-L-arginine (=L NMMA),
N5-(1-imino-3-butenyl)-L-ornithine (=Vinyl L-NIO)
N-[3-(aminomethyl)benzyl]acetamidine (=1400W)
N5-[imino(propylamino)methyl] L-ornithine (=N-Pr-L-Arg)

The results are shown in the following table, Table 3.

TABLE 3

| | IC50 value [µM] | |
|---|---|---|
| Substance | Citrulline assay (according to Bredt and Snyder (1990)) | Arginine assay according to the invention as in Example 4 |
| 7-Nitroindazole | 5.23 | 4.27 |
| TRIM | >100 | >100 |
| L-NMMA | 4.67 | 6.07 |
| Vinyl L-NIO | 5.57 | 5.02 |
| 1400 W | 16.74 | 6.98 |
| N—Pr-L-arg | 1.07 | 1.00 |

As can be seen from Table 3 the IC50 values measured by the two differing methods are very similar and, in the six substances, they differ only by a factor of 2.4 even in the most unfavourable case. This is clear proof that both methods for determining the IC50 are entirely appropriate and thus the method according to the invention is a very valid method for determining NOS inhibition, and qualitatively it is thoroughly comparable with the known standard method, the citrulline method according to Bredt and Snyder (1990), which is much more expensive on account of the column chromatography involved. In view of the fact that the method according to the invention is very much easier, more expedient and even HTS compatible, the procedure according to the invention is greatly advantageous.

We claim:

1. A high-throughput screening method for an agent that modulates NO synthase activity, the method comprising,
    (a) substantially simultaneously incubating in a plurality of reaction vessels a reaction mixture comprising NO synthase and labeled arginine as substrate, whereby arginine is converted into citrulline by the NO synthase, wherein each reaction vessel contains a candidate agent;
    (b) substantially simultaneously separating non-converted arginine from the reaction mixture in each of the plurality of reaction vessels and capturing the non-converted arginine by means of a filter plate membrane;
    (c) measuring the amount of captured arginine from each of the plurality of reaction vessels corresponding to each individual candidate agent on the filter plate membrane as an indication of the NO synthase activity; and
    (d) comparing the NO synthase activity in the presence of the candidate agent with NO synthase activity measured in the absence of the candidate agent, wherein a change in the NO synthase by virtue of the presence of candidate agent indicates that the candidate agent modulates NO synthase activity.

2. A method according to claim 1, wherein the filter plate membrane is located on an opening of the reaction vessel and the non-converted arginine is captured by suctioning the reaction mixture through the filter plate membrane.

3. A method according to claim 1, wherein the reaction mixture further comprises cofactors or coenzymes or both.

4. A method according to claim 1, wherein the filter plate membrane is a paper filter or textile filter, supported on a porous or perforated solid material made of metal, glass or ceramics.

5. A method according to claim 1, wherein the cation exchanger has functional groups that are fixed to the filter plate membrane.

6. A method according to claim 5, wherein the functional groups of the cation exchanger are phosphate, carbonate, phosphonate, sulphate or sulphonate groups.

7. A method according to claim 1, wherein the filter plate membranes are paper filters having a thickness of 10.00 mm to 0.10 mm.

8. A method according to claim 7, wherein the paper filter has a thickness of 1.00 mm to 0.15 mm.

9. A method according to claim 8, wherein the paper filter has a thickness of 0.50 mm to 0.20 mm.

10. A method according to claim 9, wherein the paper filter has a thickness of 0.23 mm.

11. A method according to claim 1, wherein the filter plate membrane is a cation exchanger with an exchange capacity of at least 1.0 µEq./cm$^2$.

12. A method according to claim 11, wherein the cation exchanger has an exchange capacity of at least 10.0 µEq./cm$^2$.

13. A method according to claim 12, wherein the cation exchanger has an exchange capacity of at least 18.0 µEq./cm$^2$.

14. A method according to claim 1, wherein the reaction vessels are wells of a microtiter plate.

15. A method according to claim 14, wherein the microtiter plate has 24, 48, 96, 384, 864 or 1536 wells.

16. A method according to claim 1, wherein the reaction vessel has a capacity of not more than 2 ml.

17. A method according the claim 16, wherein the capacity is 1 ml, 800 µl, 350 µl, 300 µl, 250 µl, 150 µl, 100 µl, 50 µl, 30 µl, or 5 µl.

18. A method according the claim 16, wherein the capacity is less than 5 µl.

19. A method according to claim 1, wherein the NO synthase activity is inhibited by the candidate agent.

20. A method according to claim 19, wherein labeled arginine is captured on the filter plate membrane.

21. A method according to claim 19, wherein the labelled arginine is bound to the filter plate membrane.

22. A method according to claim 1, wherein the arginine is labeled by radioactivity, fluorescence, or luminescence or spectrum change.

23. A method according to claim 1, wherein the arginine is labeled with radioactivity and measurement of captured non-converted arginine takes place in a scintillation counter after scintillation fluid has been added to the filter plate membrane.

24. A method according to claim 1, wherein after step (a) the reaction mixture in each of the plurality of reaction vessels is transferred to a separate corresponding plurality of reaction vessels comprising the filter plate membrane for carrying out step (b).

25. A method according to claim 1, wherein the filter plate membrane with the captured arginine is eluded with water or buffer to remove components in the reaction mixture unbound to the filter plate membrane to increase the signal/noise ratio.

26. A method according to claim 25, wherein the filter plate membrane with the captured arginine is eluded for not more than three times.

27. A method according to claim 25, wherein the filter plate membrane with the captured arginine is eluded with water or buffer of a volume of not more than 10 ml at a time.

28. A method according to claim 27, wherein the water or buffer volume is about 5 ml, about 3 ml, or about 2 ml.

29. A method according to claim 27, wherein the water or buffer volume is not less than 2 ml.

30. A method according to claim 1, wherein the NO synthase is a recombinant NO synthase.

31. A method according to claim 30, wherein the NO synthase is subtype-specific.

32. A method according to claim 31, wherein the NO synthase is human-, rat- or mouse-specific eNOS, iNOS or nNOS.

33. A method according to claim 32, wherein the NO synthase is α or β nNOS.

34. A method according to claim 1, wherein the NO synthase is part of a raw extract of vertebrate tissue.

35. A method according to claim 34, wherein the vertebrate is mammal.

36. A method according to claim 35, wherein the raw extract is a supernatant of a homogenate of rat or mouse cerebellum.

37. A method according to claim 1, wherein the separation according to step (b) takes place 1–600 min after incubation in step (a) begins.

38. A method according to claim 37, wherein the separation according to step (b) takes place 3–120 min after incubation in step (a) begins.

39. A method according to claim 38, wherein the separation according to step (b) takes place 5–60 min after incubation in step (a) begins.

40. A method according to claim 1, wherein the method has a signal-to-noise ratio of at least 4.

41. A method according to claim 40, wherein the signal-to-noise ratio is 4, 5, 6, or 10.

42. A method according to claim 40, wherein the signal-to-noise ratio is more than 10.

43. A method of measuring a NO synthase activity, comprising the steps of:
   (a) incubating NO synthase with labeled arginine as substrate in a reaction mixture contained in a reaction vessel, whereby arginine is converted into citrulline by the NO synthase,
   (b) separating nonconverted arginine from the reaction mixture and capturing non-converted arginine by means of a filter plate membrane; and
   (c) measuring the amount of captured arginine on the filter plate membrane as an indication of the NO synthase activity.

44. A screening method for an agent that modulates NO synthase activity, the method comprising,
   (a) incubating, in the presence of a candidate agent, NO synthase with labeled arginine as substrate in a reaction vessel, whereby arginine is converted into citrulline by the NO synthase;
   (b) separating non-converted arginine from the reaction mixture and capturing non-converted arginine by means of a filter plate membrane;
   (c) measuring the amount of captured arginine on the filter plate membrane as an indication of the NO synthase activity; and
   (d) comparing the NO synthase activity in the presence of the candidate agent with the NO synthase activity measured in the absence of the candidate agent, wherein a change in the NO synthase by virtue of the presence of candidate agent indicates that the candidate agent modulates NO synthase activity.

* * * * *